United States Patent
Zesiewicz et al.

(10) Patent No.: US 11,304,650 B1
(45) Date of Patent: Apr. 19, 2022

(54) SYSTEMS AND METHODS FOR HEEL-TO-SHIN TESTING

(71) Applicant: UNIVERSITY OF SOUTH FLORIDA, Tampa, FL (US)

(72) Inventors: Theresa Ann Zesiewicz, Oldsmar, FL (US); Kyle Brandon Reed, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 341 days.

(21) Appl. No.: 16/358,852

(22) Filed: Mar. 20, 2019

(51) Int. Cl.
*A61B 5/00* (2006.01)
*A61B 5/11* (2006.01)

(52) U.S. Cl.
CPC .......... *A61B 5/4076* (2013.01); *A61B 5/0048* (2013.01); *A61B 5/1124* (2013.01); *A61B 5/4064* (2013.01); *A61B 5/4824* (2013.01); *A61B 5/6828* (2013.01); *A61B 5/11* (2013.01); *A61B 5/6801* (2013.01); *A61B 5/6829* (2013.01); *A61B 5/6831* (2013.01); *A61B 2562/0247* (2013.01); *A61B 2562/0252* (2013.01); *A61B 2562/0261* (2013.01); *A61B 2562/046* (2013.01); *A61B 2562/164* (2013.01)

(58) Field of Classification Search
CPC ... A61B 5/4076; A61B 5/0048; A61B 5/4064; A61B 5/6828; A61B 5/4824; A61B 2562/0247; A61B 2562/0261; A61B 2562/0252; A61B 2562/164; A61B 5/6831; A61B 5/11; A61B 5/6801; A61B 2562/046; A61B 5/6829
See application file for complete search history.

(56) References Cited

U.S. PATENT DOCUMENTS

| | | | |
|---|---|---|---|
| 4,062,355 A | 12/1977 | Kaye | |
| 5,476,103 A | 12/1995 | Nahsner | |
| 6,050,962 A * | 4/2000 | Kramer | A61B 5/1071 600/595 |
| 6,692,449 B1 | 2/2004 | Brown | |
| 8,827,718 B2 | 9/2014 | Chiu | |
| 9,050,199 B1 * | 6/2015 | Reed | A61F 2/64 |

(Continued)

FOREIGN PATENT DOCUMENTS

KR 101338049 B1 11/2012

OTHER PUBLICATIONS

NYU School of Medicine, The Precise Neurological Exam, Coordinate, Gait and Rhomberg Test, https://web.archive.org/web/20191205075405/https://informatics.med.nyu.edu/modules/pub/neurosurgery/coordination.html (Year: 2018).*

*Primary Examiner* — Sean P Dougherty
(74) *Attorney, Agent, or Firm* — Quarles & Brady LLP

(57) ABSTRACT

In one embodiment, a system for heel-to-shin testing includes a patient interface configured to be applied to a shin of a patient and extend from a point on the shin adjacent the knee to a point on the shin adjacent the ankle, the patient interface including an elongated medial touch sensor configured to sense contact of a heel of the patient to a centerline of the shin at any axial position between the knee and the ankle, and a control module in electrical communication with the patient interface, the control module being configured to identify a number of times the patient's heel deviates from the centerline of the shin as the patient slides the heel down the shin or drags the heel up the shin.

18 Claims, 5 Drawing Sheets

(56) References Cited

U.S. PATENT DOCUMENTS

| | | | |
|---|---|---|---|
| 9,763,848 B1* | 9/2017 | Handzic | A61H 3/0288 |
| 9,990,333 B1* | 6/2018 | Reed | A61F 2/5046 |
| 2007/0275957 A1* | 11/2007 | Weiner | A61K 31/5415 |
| | | | 514/225.5 |
| 2008/0306407 A1* | 12/2008 | Taylor | A61B 5/6828 |
| | | | 600/587 |
| 2009/0024062 A1* | 1/2009 | Einarsson | A61F 5/01 |
| | | | 600/595 |
| 2009/0043170 A1* | 2/2009 | Sulkin | A61B 5/1126 |
| | | | 600/300 |
| 2009/0299227 A1* | 12/2009 | Thaler | A61B 5/0002 |
| | | | 600/587 |
| 2011/0055753 A1* | 3/2011 | Horodezky | G06F 3/04883 |
| | | | 715/810 |
| 2011/0208444 A1* | 8/2011 | Solinsky | A61B 5/1122 |
| | | | 702/41 |
| 2011/0319787 A1* | 12/2011 | Lamoise | A61B 5/103 |
| | | | 600/549 |
| 2013/0192071 A1* | 8/2013 | Esposito | A43D 1/027 |
| | | | 33/6 |
| 2013/0276317 A1* | 10/2013 | Smirman | A61B 5/0079 |
| | | | 33/515 |
| 2014/0213929 A1* | 7/2014 | Dunbar | A61B 5/743 |
| | | | 600/557 |
| 2014/0288383 A1* | 9/2014 | Barnett | G01N 27/00 |
| | | | 600/301 |
| 2014/0296749 A1* | 10/2014 | Reid, Jr. | D04B 1/12 |
| | | | 600/587 |
| 2015/0297132 A1* | 10/2015 | Bichel | A61B 5/4836 |
| | | | 600/301 |
| 2016/0120733 A1* | 5/2016 | Ishikawa | A43B 3/0005 |
| | | | 601/151 |
| 2016/0157779 A1* | 6/2016 | Baxi | A61B 5/6831 |
| | | | 600/301 |
| 2016/0338621 A1* | 11/2016 | Kanchan | A61B 5/002 |
| 2017/0025033 A1* | 1/2017 | Rath | A61B 5/103 |
| 2017/0071816 A1* | 3/2017 | Vain | A61F 5/0123 |
| 2017/0079868 A1* | 3/2017 | Reid, Jr. | D04B 1/265 |
| 2017/0089782 A1* | 3/2017 | Hirt | A61B 5/01 |
| 2017/0100300 A1* | 4/2017 | Rapp | A61B 5/6824 |
| 2017/0265810 A1* | 9/2017 | Van De Vyver | A61B 5/6833 |
| 2017/0273623 A1* | 9/2017 | Chen | A61B 5/0022 |
| 2018/0028096 A1* | 2/2018 | Katz | A61B 5/1112 |
| 2018/0160940 A1* | 6/2018 | Kim | A61B 5/45 |
| 2018/0220966 A1* | 8/2018 | Cohen | A61B 5/7425 |
| 2019/0117156 A1* | 4/2019 | Howard | A61B 5/4585 |
| 2019/0200915 A1* | 7/2019 | Baker | A61B 5/4088 |
| 2020/0178849 A1* | 6/2020 | Cheng | A43B 3/0005 |
| 2020/0367823 A1* | 11/2020 | Chahine | A61B 5/1116 |
| 2020/0371675 A1* | 11/2020 | Sung | G06F 3/04845 |
| 2021/0022666 A1* | 1/2021 | Malawey | A61B 5/742 |

\* cited by examiner

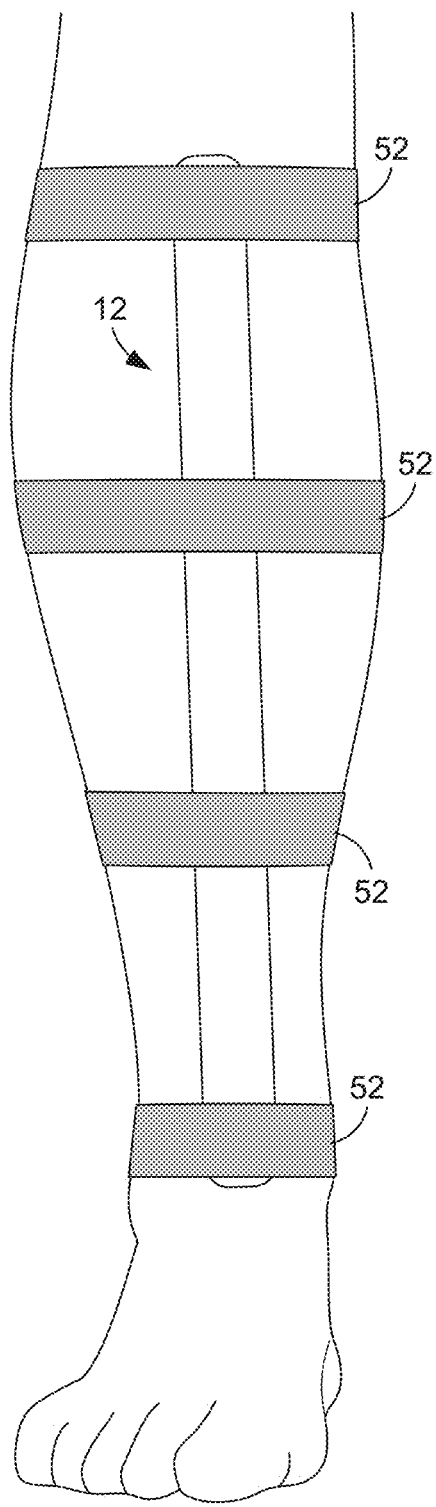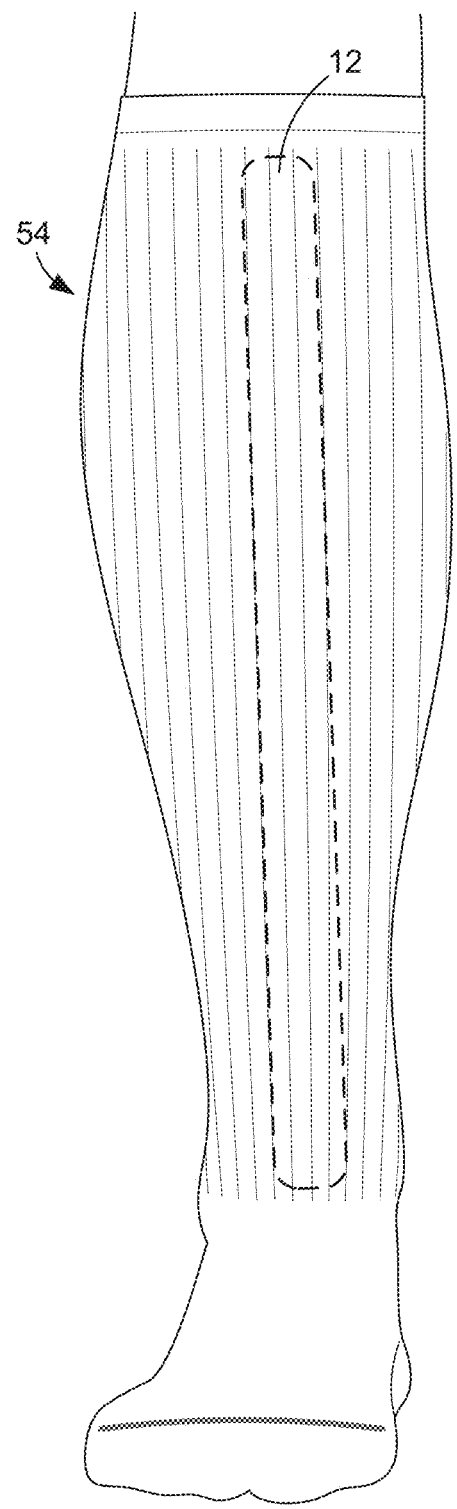
FIG. 6  FIG. 7

SYSTEMS AND METHODS FOR HEEL-TO-SHIN TESTING

BACKGROUND

The heel-to-shin test is a test of lower limb coordination and position sense, and is often used to evaluate the integrity of the cerebellum. In the test, a supine or seated patient is requested to place the heel of one foot at the top of the shin just below the knee of the opposite leg, slide the heel down the center of the shin toward the ankle, and then drag the heel back up to the knee. The patient may perform this action several times with both heels, each sliding along the shin of the opposite leg. As the patient performs the test, a medical practitioner (e.g., physician, nurse, or physical therapist) identifies the number of times that the patient's heel deviates from the center of the shin, this number being indicative of the health of the cerebellum.

While this form of testing can provide the practitioner with an idea of the functioning of the patient's cerebellum, it is imprecise as it relies on the practitioner's subjective impressions as to whether or not the heel deviates from the center of the shin to an extent to which the occurrence should actually be counted as a deviation. As one can imagine, one practitioner may count slight movements from the center of the shin as deviations that should be noted, while another practitioner may only count larger movements from the center of the shin as deviations that should be noted. Because of this subjectivity, the results of the test are of less value than they could be and are not very useful for comparison with the results of other heel-to-shin tests administered by other practitioners.

In view of the subjectivity of the current heel-to-shin testing, it can be appreciated that it would be desirable to have systems and methods for heel-to-shin testing that are more precise and yield more useful results.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 6 is a front view of the lower leg illustrating a first example of application of the patient interface to the leg.

FIG. 7 is a front view of the lower leg illustrating a second example of application of the patient interface to the leg.

DETAILED DESCRIPTION

As described above, it would be desirable to have systems and methods for heel-to-shin testing that are precise and yield useful results. Disclosed herein are examples of such systems and methods. In one embodiment, a system for heel-to-shin testing comprises a patient interface that can be applied to a patient's shin. The patient interface includes at least one elongated touch sensor that can be positioned over the medial portion of the patient's shin from the knee to the ankle. The system can further include a control module that is in electrical communication with the touch sensor and that can collect data from it. The data that is collected depends upon the nature of the touch sensor. In cases in which the touch sensor is only configured to detect contact, the data includes the number of times the heel deviates from the medial shin, which can be identified from the number instances in which contact is interrupted. In cases in which the touch sensor detects contact as well as the position at which the contact occurs, the data includes the number of times the heel deviates from the shin as well as the axial positions at which such deviations occurred. In such a case, the nature of the deviations can be identified and the percentage of the total distance and/or time that the heel is or is not correctly aligned with the shin can be determined.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

The disclosed systems and methods enable more precise heel-to-shin testing by electronically sensing contact between the patient's heel and the shin of the patient's opposite leg. Such sensing removes the opportunity for judgement errors or subjectivity on the part of the individual (e.g., medical practitioner) administering the test. Accordingly, more accurate results can be obtained and, therefore, more accurate assessments can be made about the functioning of the patient's cerebellum.

Figure 1:
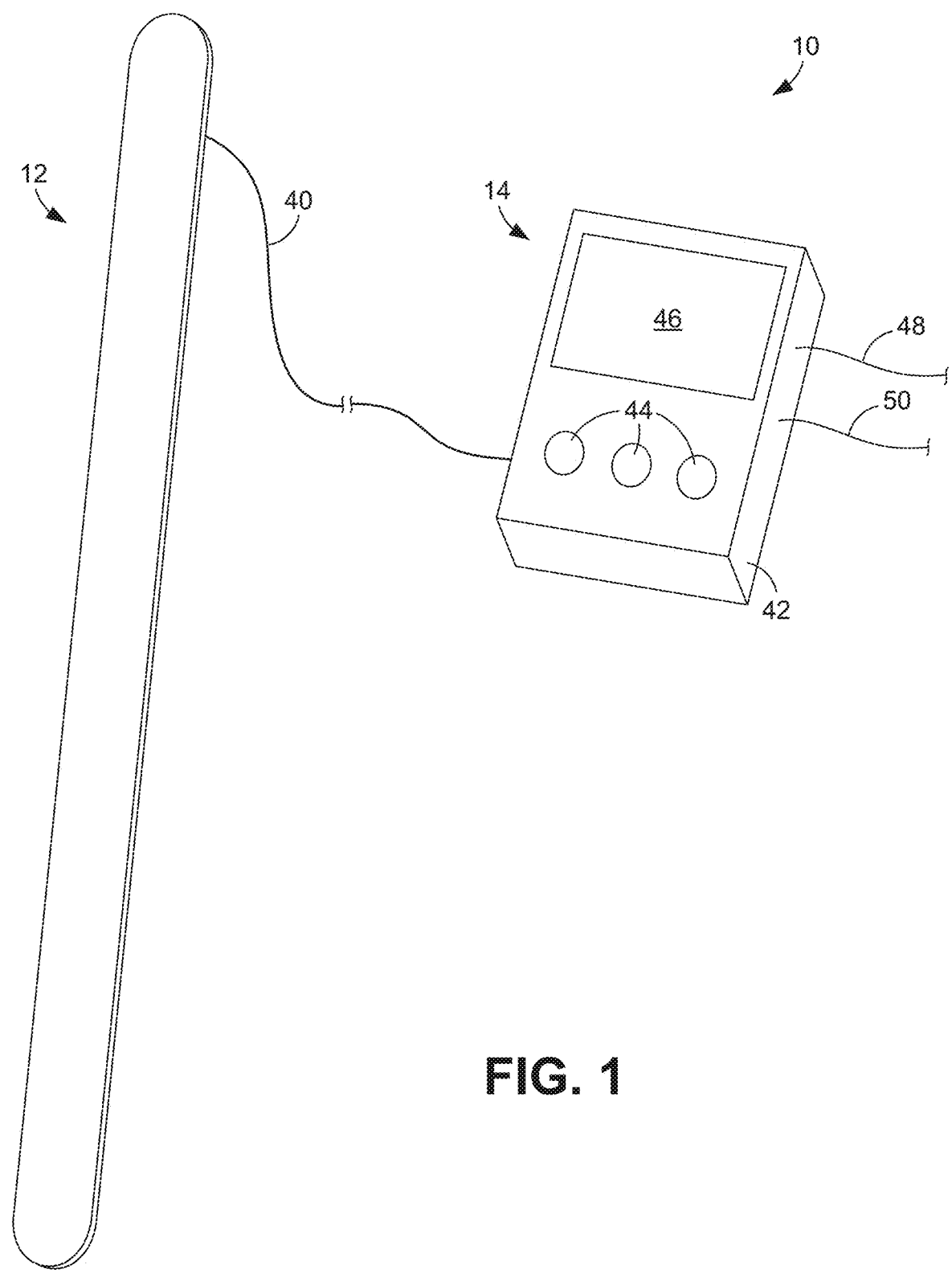
FIG. 1 is a schematic view of an embodiment of a system for heel-to-shin testing.
Figure 2:
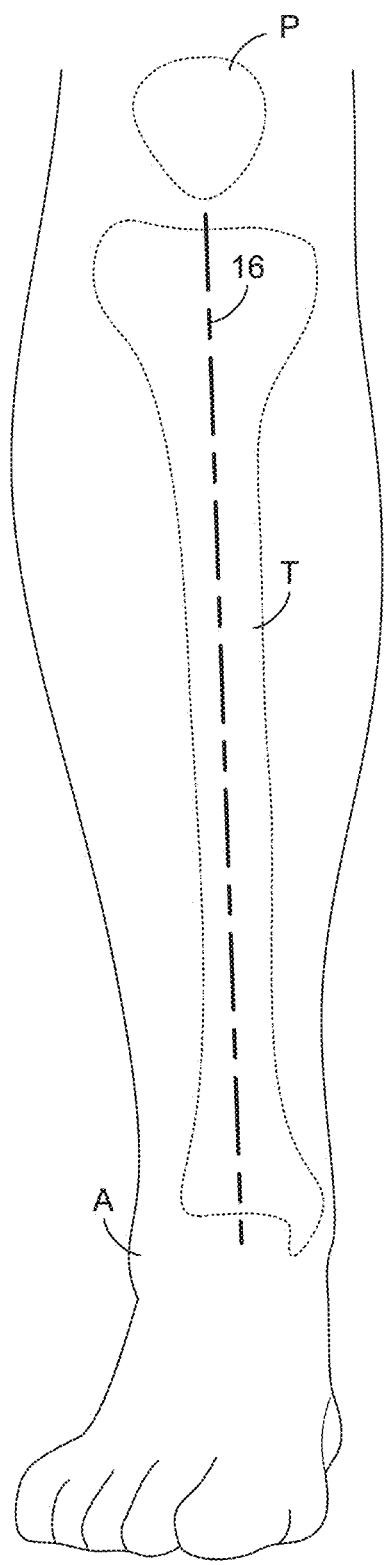
FIG. 2 is a front view of the lower leg that illustrates an example of the positioning of a patient interface of the system of FIG. 1 on the shin.

FIG. 1 illustrates an example embodiment of a system 10 for heel-to-shin testing. As shown in this figure, the system 10 generally comprises a patient interface 12 and a control module 14. The patient interface 12 is configured to be applied to a patient's shin and extend from the knee to the ankle. As shown in FIG. 1, the patient interface can be configured as an elongated, narrow, thin strip. The patient interface 12 can be made of a flexible material, such as a polymeric material, so that it can conform to the contours of the patient's shin. FIG. 2 illustrates an example of placement of the patient interface 12. The patient interface 12 can overlie an axial centerline of the shin, the location of which is identified by the line 16. This centerline can coincide with the axial centerline of the tibia, T, and can extend from a point just below the patella, P, down to the ankle, A. While location of the centerline is identified with the line 16 in FIG. 2, it is to be understood that this line is only used to identify the location of the centerline and that the "centerline" that the patient is to slide or drag his or her heel along during the heel-to-shin test actually has a width that is generally equal to the width of an elongated medial touch sensor that overlies the axial centerline of the shin. As described below, the elongated touch sensor is configured to detect contact from the heel of the patient's other leg and extends along substantially the entire length of the patient interface 12 and, therefore, also spans the shin from the knee to the ankle.

Figure 3:
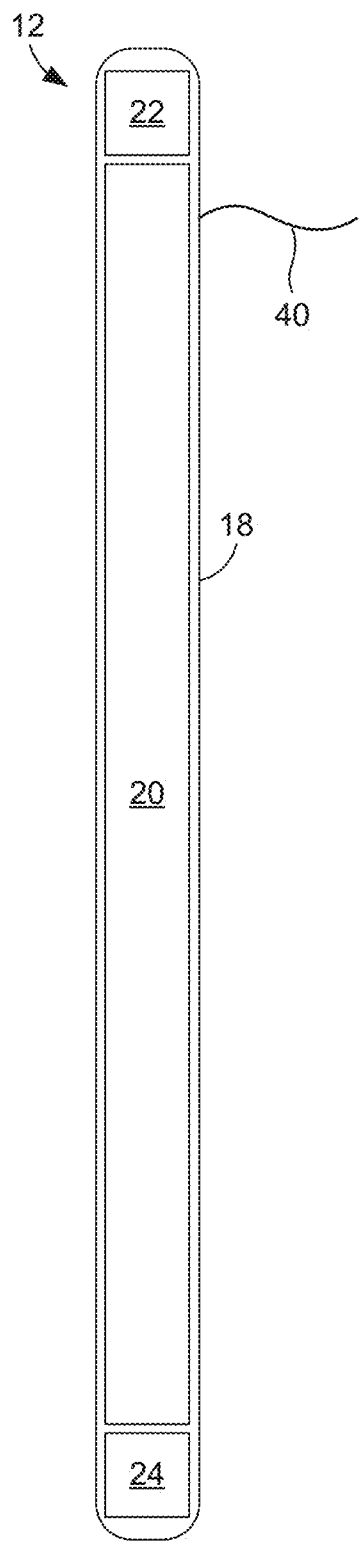
FIG. 3 is a front view of a first embodiment for a patient interface that can be used in the system of FIG. 1.

FIG. 3 shows a first embodiment for the patient interface 12. In this embodiment, the patient interface 12 comprises a flexible substrate 18 that supports an elongated medial touch sensor 20 that nearly extends along the entire length of the substrate and, therefore, is configured to extend along the patient's shin from the knee to the ankle. The length of the medial touch sensor 20 can be selected to accommodate the length of the shin with which it is to be used. In some embodiments, multiple sizes of patient interfaces 12 and, therefore, medial touch sensors 20, can be manufactured and the appropriate size can be selected based upon the size of the patient. The same can be true for the width of the medial touch sensor 20 and, therefore, the width of the "centerline" of the shin used in the testing. As the width of the centerline is generally equal to the width of the medial touch sensor 20, the width of the medial touch sensor can be varied to vary the width of the centerline and, therefore, the degree of difficulty in maintaining the heel in the correct location as is slide along the shin. In most embodiments, however, the medial touch sensor 20 will have a width of approximately 1 to 3 cm. Provided on the substrate 18 above and below the medial touch sensor 20 (in the orientation of the figure) are top and bottom touch sensors 22 and 24. As described below, the top and bottom touch sensors 22, 24 can be used to identify the location of the patient's heel in the case in which the medial touch sensor 20 is only configured to detect contact and cannot detect the position at which that contact is made. In such a case, the patient can begin the heel-to-shin test by touching his or her heel to the top sensor 22 just below the knee, slide the heel down the shin to the bottom sensor 24 near the ankle, and then drag the heel back up the shin to the top sensor to complete one full cycle of the test. By contacting the top and bottom sensors 22, 24 in this manner, the system 10 can track the patient's progress in performing the test despite the medial touch sensor 20 not being configured to detect the position of the heel's contact.

Figure 4:
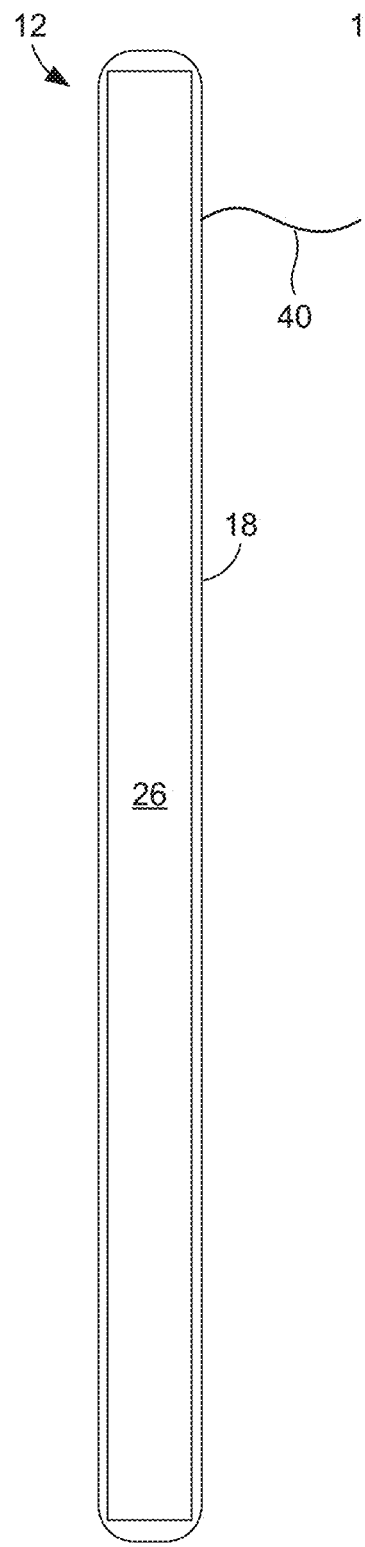
FIG. 4 is a front view of a second embodiment for a patient interface that can be used in the system of FIG. 1.

FIG. 4 shows a second embodiment for the patient interface 12. In this embodiment, the patient interface 12 comprises a flexible substrate 18 that supports only a medial touch sensor 26. In this case, however, the touch sensor 26 is configured to both detect contact and the position at which the contact is made so that the point at which the heel touches the sensor can be determined at any given time. Because the touch sensor 26 can detect position, there is no need for the additional top and bottom touch sensors shown in FIG. 3.

Figure 5:
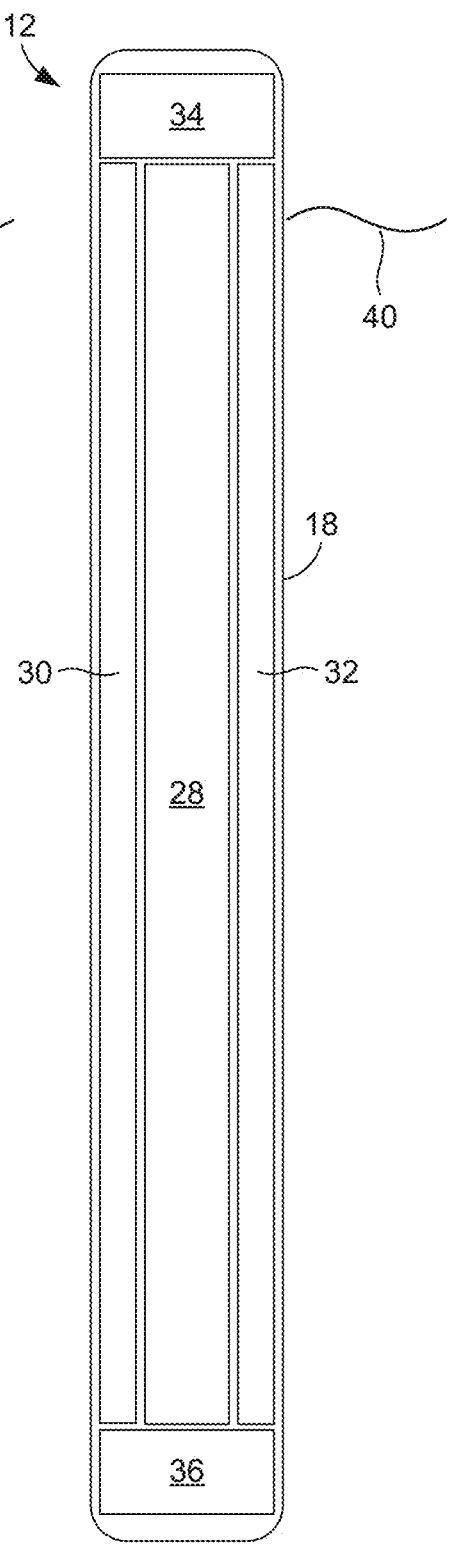
FIG. 5 is a front view of a third embodiment for a patient interface that can be used in the system of FIG. 1.

FIG. 5 shows a third embodiment for the patient interface 12. In this embodiment, the patient interface 12 comprises a flexible substrate 18 that supports an elongated medial touch sensor 28 and two elongated lateral touch sensors 30 and 32 that are positioned on either lateral side of the medial touch sensor and also extend nearly the entire length of the substrate. In such an embodiment, the patient interface 12 is configured not only to detect positive contact between the heel and the centerline of the shin (which is the goal of the heel-to-shin test), but also positive contact between the heel and the sides of the shin and, therefore, lateral deviation from the centerline of the shin. In the illustrated example, it is assumed that neither the medial touch sensor 28 nor the lateral touch sensors 30, 32 can detect the position at which contact is made. Because of this, the patient interface 12 further includes top and bottom touch sensors 34 and 36 as in the embodiment of FIG. 3. It is noted, however, that these additional touch sensors 34, 36 can be omitted if at least the medial touch sensor 28 can detect position.

The touch sensors comprised by the patient interface can take a variety of forms. In some embodiments, the touch sensor 26 comprises at least one force transducer that, for example, comprises one or more strain gauges, piezoelectric elements, resistive elements, or a capacitive elements. The touch sensors can register contact by the heel when the heel is pressed against the sensor with a force that meets or exceeds a predetermined threshold.

With reference back to FIG. 1, the patient interface 12 and, more particularly, the touch sensor(s) it supports, is placed in electrical communication with the control module 14 with a cable 40. The control module 14 is used to control operation of the system 10 and to collect data, in the form of contact and possibly the location of such contact, sensed by the touch sensors. As shown in FIG. 1, the control module 14 can comprise an outer housing 42 that supports a user interface that includes user input devices, such as one or more buttons 44, and a display 46, which can, for example, comprise a liquid crystal display (LCD). The buttons 44 can be used to control operation of the system 10 as a whole and the display 46 can be used to convey information collected by the system to the user (e.g., medical practitioner), as described below. An example configuration for the control module 14 is described below with reference to FIG. 8.

Also shown in FIG. 1 are two further cables 48 and 50 that extend from the control module 14. One of these cables 48 can be used to deliver power (e.g., voltage from a wall outlet) to the control module 14 and the other cable 50 can be used to transmit data to a separate computing device (not shown), such as a desktop computer, notebook computer, tablet computer, smart phone, or other device with computing capability.

In order to conduct heel-to-shin testing, the patient interface 12 must be applied to the shin. To prevent slippage, it is desirable to attach the patient interface 12 to the shin. Such attachment can be achieved in a variety of ways. In one embodiment, the patient interface 12 can be secured to the shin with adhesive tape that lines its back side. In another embodiment, the patient interface 12 can be secured to the shin using flexible, possibly elastic, bands 52, as depicted in FIG. 6. The bands 16 can be made of a flexible material, such as a fabric or polymeric material, and, in some embodiments, can be elastic. The bands 18 can comprise continuous (endless) bands that can be slid over the patient's leg, or can be a non-continuous band, in which case the band has opposed free ends that can be connected together with suitable fastening elements, such as hook and loop fasteners, snaps, a buckle, or the like.

In yet another embodiment, the patient interface 12 can be secured to the shin using a stocking 54, as depicted in FIG. 7. In such a case, the patient interface 12 can simply be placed between the material of the stocking 54 and the patient's shin. If the stocking 54 is sufficiently elastic, it can hold the patient interface 12 in place for long enough to conduct the heel-to-shin testing. In a variation, the stocking 54 can be specifically configured to support the patient interface 12. For example, the stocking 54 can comprise a pocket, integral straps, or other suitable means to hold the patient interface 12 in place. It is noted that while a "stocking" has been identified, an elastic sleeve, which is similar to a stocking but without a foot portion, could also be used.

Figure 8:
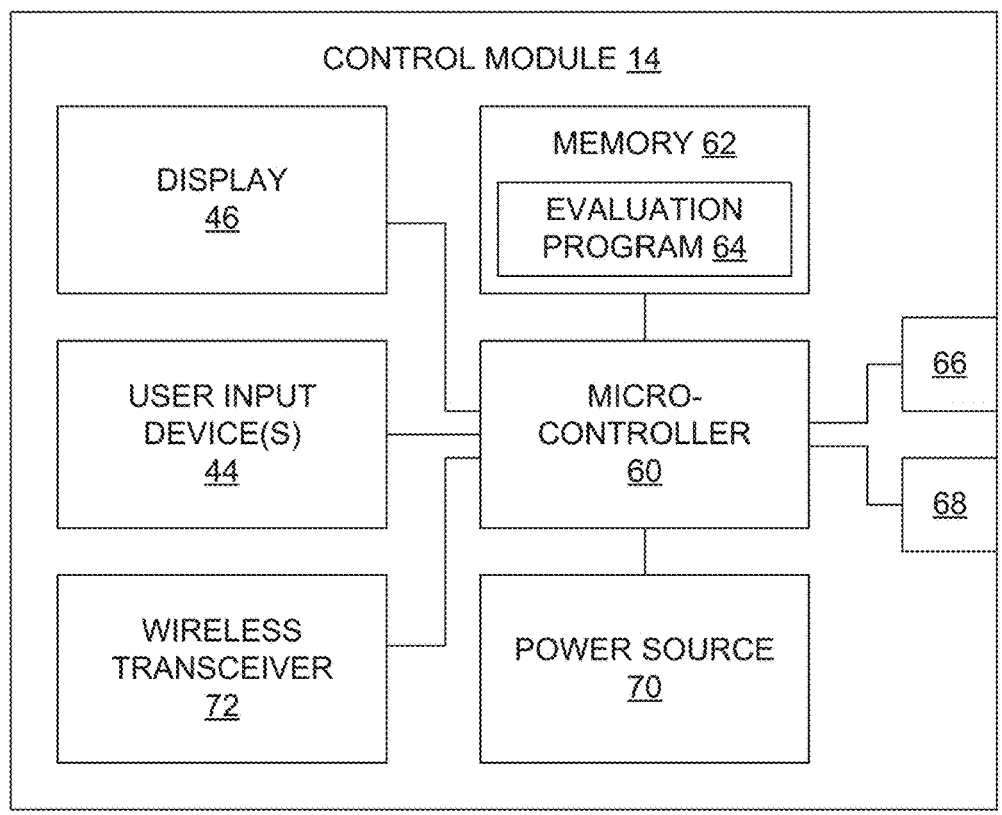
FIG. 8 is a block diagram of an embodiment of the architecture of a control module shown in FIG. 1.

FIG. 8 shows an example architecture for the control module 14. As shown in this figure, in addition to the user input devices (e.g., buttons) 44 and the display 46, the control module 14 can include a microcontroller 60 that controls the operation of the system 10 and memory 62 that stores an evaluation program 64 configured to initiate an evaluation session in which the heel is to be slid down and dragged up the centerline of the shin of the opposite leg and to track the number of times the heel deviates from the centerline of the shin from data provided by the touch sensor(s) of the patient interface. While the memory 62 is shown as a separate component from the microcontroller 60, it will be appreciated that the memory can, in some embodiments, be integrated with the microcontroller. In addition, the memory 62 can comprise a removable computer-readable medium, such as a memory card.

Also shown in FIG. 8 are electrical ports 66 and 68 that can be used for connection with the cables 48 and 50 shown in FIG. 1. In addition, shown are an optional power source 70, such as a battery, which can be used to power the control module 14, and an optional wireless transceiver 72, which can be used to wirelessly transmit data to the separate computing device.

The system 10 can be used to conduct heel-to-shin tests similar to those performed in the prior art, but with much greater precision and accuracy. To conduct such a test, the control module 14 is powered on, for example, by pressing one of the buttons 44 (e.g., a "power" button). The patient interface 12 is then (or previously) applied to the shin of the patient in a manner in which the interface extends from the knee to the ankle along the centerline of the shin.

Once the patient interface 12 has been applied to the patient's shin, an evaluation session can be conducted. The patient, who may be lying supine or sitting, places the heel of one foot against the top of the shin of the opposite leg. Assuming the patient is able to place the heel in the correct position, a touch sensor of the patient interface 12 detects contact between the heel and the shin. Which touch sensor detects this contact depends upon the configuration of the patient interface 12. If the patient interface 12 is one that comprises a separate top sensor, such as sensor 22 shown in FIG. 3, it is that sensor that detects the contact. If no such top sensor is provided, however, it is the elongated medial touch sensor that detects the contact. In the latter case, the medial touch sensor also detects the position at which the contact is made. When such contact is made, the control module 14 can automatically initiate an evaluation session and begin noting when deviations occur. Alternatively, the control module 14 can be manually initiated using a button 44 provided on the module (e.g., a "start" button).

Figure 9:
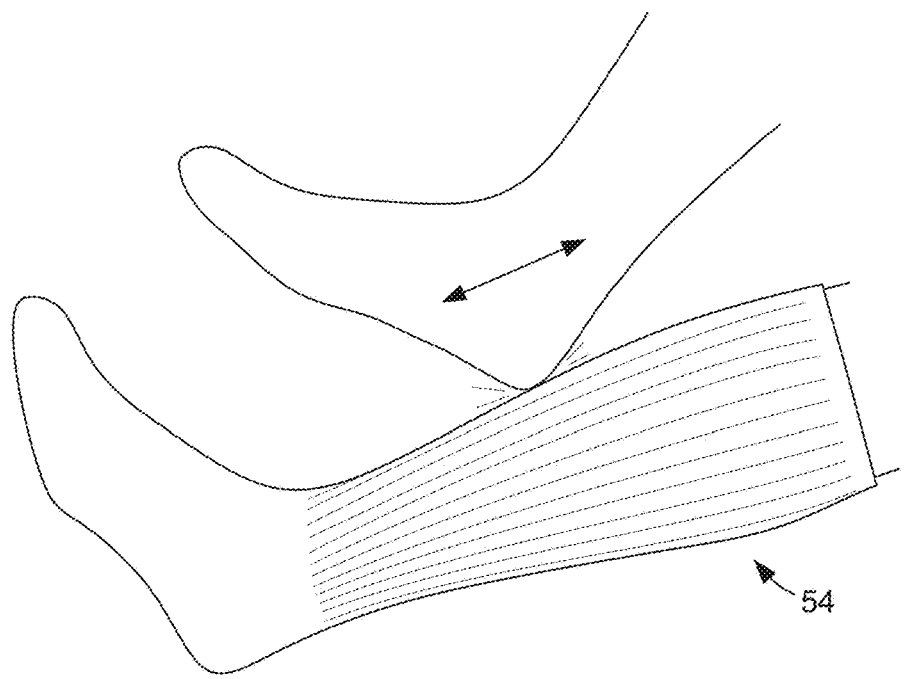
FIG. 9 is a side view illustrating a patient performing a heel-to-shin test using a stocking that incorporates the patient interface.

Next, the patient slowly slides his or her heel down the shin while trying to keep the heel in the centerline of the shin, where the medial touch sensor is located. FIG. 9 illustrates an example of this process. If the patient's heel does not deviate from the centerline of the shin, as defined by the width of the medial touch sensor, as the heel is slid down the shin, this contact will be continuous. If the patient's heel deviates from the centerline of the shin, however, the contact with the medial touch sensor will be interrupted. In such a case, the control module 14 receives this information and registers deviations. If the patient interface 12 includes lateral touch sensors, as in the embodiment of FIG. 5, the control module 14 also receives an indication from one of the lateral touch sensors and can, therefore, determine the direction in which the deviation occurred. If the medial touch sensor is capable of sensing the location of contact by the heel, the control module 14 also receives this information.

If the patient deviates from the centerline of the shin but corrects and returns the shin to the centerline of the shin to continue the test, this re-established contact is detected by the medial touch sensor. Any further deviations from the centerline of the shin will again be detected in similar manner to that described above. Accordingly, both in the downward stroke and upward stroke of the heel, the control module 14 can count the number of times the heel deviates from the centerline of the shin with great precision and accuracy. In addition, the control module 14 can determine the positions along the shin at which contact is made or lost and, potentially, in what direction each deviation occurred. Furthermore, the control module 14 can calculate the total percentage of distance along the shin or time during the evaluation that the heel either is or is not in proper alignment with the centerline of the shin. Accordingly, the system 10 collects all the information normally collected by the prior art heel-to-shin test as well as other information that may be valuable to the medical practitioner. The information gleaned by the system can be displayed in the display 46, stored within memory 62, and/or transmitted to the separate computing device.

It is also noted that the disclosed system can further include components that are used to conduct other evaluations relevant to a patient's brain or neurological system health. For example, appropriate vibration elements can be integrated into the stocking to evaluate the patient's ability to sense vibrations for the purpose of performing a neurologic vibratory sense evaluation.

The invention claimed is:

1. A system for heel-to-shin testing, the system comprising:
    a patient interface configured to be attached to a shin of a patient, the patient interface comprising an elongated flexible substrate sized and configured to extend from a point on the shin adjacent the knee to a point on the shin adjacent the ankle, the patient interface including an elongated medial touch sensor configured to sense contact of a heel of the patient along a centerline of the shin at any axial position between the knee and the ankle and further configured to sense the axial position at which the contact occurs, the medial touch sensor being approximately 1 to 3 cm wide, the patient interface further including first and second elongated lateral touch sensors positioned to the left and right of the medial touch sensor, the lateral touch sensors being configured to sense contact of the heel when the heel deviates from the centerline of the shin; and
    a control module in electrical communication with the patient interface, the control module including a microcontroller, memory that stores an evaluation program configured for execution by the microcontroller, a user interface configured to receive user commands, and a display configured to communicate information about the testing to the user, wherein the control module is configured to count a number of times the patient's heel deviates from the centerline of the shin as the patient slides the heel down the shin and drags the heel up the shin, the control module further being configured to calculate a percentage of time or distance that the heel is or is not in contact with the centerline of the shin as the heel is slid down or dragged up the shin.

2. A system for heel-to-shin testing, the system comprising:
    a patient interface configured to be applied to a shin of a patient and extend from a point on the shin adjacent the knee to a point on the shin adjacent the ankle, the patient interface including an elongated medial touch sensor configured to sense contact of a heel of the patient to a centerline of the shin at any axial position between the knee and the ankle; and
    a control module in electrical communication with the patient interface, the control module being configured to identify a number of times the patient's heel deviates from the centerline of the shin as the patient slides the heel down the shin or drags the heel up the shin.

3. The system of claim 2, wherein the patient interface further comprises a top touch sensor positioned above the medial touch sensor and a bottom touch sensor positioned below the medial touch sensor, the top and bottom touch sensors being configured to sense contact of the heel.

4. The system of claim 2, wherein the patient interface further comprises first and second elongated lateral touch sensors positioned to the left and right of the medial touch sensor, the lateral touch sensors being configured to sense contact of the heel.

5. The system of claim 2, wherein the medial touch sensor is further configured to sense an axial position at which contact is made by the heel.

6. The system of claim 5, wherein the control module is configured to calculate a percentage of time or distance that the heel is in or out of contact with the centerline of the shin as the heel is slid down or dragged up the shin.

7. The system of claim 2, further comprising bands configured to secure the patient interface to the patient's shin.

8. The system of claim 2, further comprising a stocking configured to secure the patient interface to the patient's shin.

9. The system of claim 2, wherein the control module comprises a microcontroller and memory that stores an evaluation program configured to count the number of times the patient's heel deviates from the centerline of the shin.

10. The system of claim 9, wherein the control module further comprises a user interface configured to receive user commands and a display configured to communicate the number of times to the user.

11. A method for heel-to-shin testing, the method comprising:
    applying an elongated medial touch sensor to a shin of a patient using at least one of adhesive tape, flexible bands, or a stocking, with the touch sensor overlying the shin from a point adjacent the knee to a point adjacent the ankle, the touch sensor being configured to sense contact between a heel of the patient and a centerline of the shin;
    electronically sensing each time the patient's heel deviates from the centerline of the shin as the patient slides the heel down the shin or drags the heel up the shin; and
    determining a total number of times the heel deviates from the centerline.

12. The method of claim 11, wherein applying an elongated medial touch sensor to a shin of a patient comprises attaching the medial touch sensor with adhesive tape.

13. The method of claim 11, wherein applying an elongated medial touch sensor to a shin of a patient comprises attaching the medial touch sensor with flexible bands.

14. The method of claim 11, wherein applying an elongated medial touch sensor to a shin of a patient comprises applying the medial touch sensor with a stocking.

15. The method of claim 11, wherein electronically sensing each time the deviates from the centerline of the shin comprises sensing the deviations with elongated lateral touch sensors positioned to the left and right of the medial touch sensor.

16. The method of claim 11, further comprising electronically sensing an axial position along the centerline at which contact is made by the heel.

17. The method of claim 16, further comprising calculating a percentage of time or distance that the heel is in or out of contact with the centerline of the shin as the heel is slid down or dragged up the shin.

18. A method for heel-to-shin testing, the method comprising:
    receiving an output from a patient sensor that is disposed on a patient's body from a point on the shin adjacent the knee to a point on the shin adjacent the ankle, the patient sensor including an elongated medial touch sensor that is configured to sense contact between a heel of the patient and a centerline of the shin at any axial position between the knee and the ankle;
    electronically sensing each time the patient's heel deviates from the centerline of the shin as the patient slides the heel down the shin or drags the heel up the shin; and
    determining with a control module a number of times the heel deviates from the centerline, and outputting the result for display to a user.

\* \* \* \* \*